(12) United States Patent
Deneuvillers

(10) Patent No.: US 9,833,266 B2
(45) Date of Patent: Dec. 5, 2017

(54) IMPLANTABLE VERTEBRAL ARTHRODESIS DEVICE FOR FUSING TWO OVERLYING AND UNDERLYING VERTEBRAE

(71) Applicant: COUSIN BIOTECH, Wervicq Sud (FR)

(72) Inventor: Guy Deneuvillers, Merlimont (FR)

(73) Assignee: COUSIN BIOTECH, Wervicq Sud (FR)

( * ) Notice: Subject to any disclaimer, the term of this patent is extended or adjusted under 35 U.S.C. 154(b) by 0 days.

(21) Appl. No.: 15/027,282

(22) PCT Filed: Oct. 7, 2014

(86) PCT No.: PCT/FR2014/052543
§ 371 (c)(1),
(2) Date: Apr. 5, 2016

(87) PCT Pub. No.: WO2015/052431
PCT Pub. Date: Apr. 16, 2015

(65) Prior Publication Data
US 2016/0242821 A1     Aug. 25, 2016

(30) Foreign Application Priority Data
Oct. 7, 2013   (FR) ..................................... 13 59691

(51) Int. Cl.
*A61B 17/70* (2006.01)
*A61F 2/44* (2006.01)
*A61F 2/30* (2006.01)

(52) U.S. Cl.
CPC ........ *A61B 17/7062* (2013.01); *A61F 2/4405* (2013.01); *A61F 2002/30622* (2013.01); *A61F 2002/4475* (2013.01)

(58) Field of Classification Search
CPC ............ A61B 17/7047; A61B 17/7062; A61B 17/7065; A61B 17/7067; A61B 17/7068;
(Continued)

(56) References Cited

U.S. PATENT DOCUMENTS 8,292,923 B1 * 10/2012 Arnold ............... A61B 17/7062
606/249
2007/0162005 A1 * 7/2007 Peterson ............ A61B 17/7062
606/279
(Continued)

FOREIGN PATENT DOCUMENTS

WO        2005/044118 A1     5/2005

*Primary Examiner* — Lynnsy Summitt
(74) *Attorney, Agent, or Firm* — MH2 Technology Law Group, LLP

(57) ABSTRACT

The present invention relates to an implantable vertebral arthrodesis device (1) for fusing an overlying vertebra and an underlying vertebra, the device comprising an anterior portion (2) having upper and lower bearing zones (2a, 2b) suitable respectively for receiving lower and upper portions (3, 6) of upper and lower laminae (4, 7) of the overlying and underlying vertebrae (5, 8), said zones (2a, 2b) being spaced apart by a minimum height h (h1) for maintaining intervertebral spacing; rigid retaining devices (9) arranged relative to the anterior portion (2) so as to block migration of said anterior portion (2) towards the spinal canal; a posterior portion (10) in connection with said anterior portion (2), including a main housing (11) having first and second openings (11a, 11b) facing each other and suitable for receiving in part the spinous processes (12, 13); and a granular osteosynthesis material arranged in said main housing (11).

17 Claims, 4 Drawing Sheets

(58) Field of Classification Search
CPC .............. A61B 17/707; A61B 17/7071; A61B 17/7097; A61B 17/885; A61B 17/8852; A61B 17/8858
See application file for complete search history.

(56) References Cited

U.S. PATENT DOCUMENTS

| | | |
|---|---|---|
| 2007/0191837 A1 | 8/2007 | Trieu |
| 2009/0018658 A1* | 1/2009 | Garcia ................ A61B 17/7062 623/17.11 |
| 2012/0215262 A1 | 8/2012 | Culbert |
| 2015/0012040 A1 | 1/2015 | Agarwal et al. |
| 2015/0282944 A1* | 10/2015 | Guizzardi ............ A61B 17/025 623/17.16 |

* cited by examiner

IMPLANTABLE VERTEBRAL ARTHRODESIS DEVICE FOR FUSING TWO OVERLYING AND UNDERLYING VERTEBRAE

BACKGROUND OF THE INVENTION

The present invention relates to the technical field of implantable vertebral arthrodesis devices for fusing together an overlying vertebra and an underlying vertebra.

The term "arthrodesis" is used to cover any fusing of a joint. Such implantable devices serve to distribute loads and overloads between two adjacent vertebrae (referred to herein as the overlying and the underlying vertebrae) as occurs as a result of degeneration of a disk (in particular in the event of a herniated disk). By way of example, in the event of degenerative disk disease, a stress or a lesion can lead to the disk tearing or to a protuberance forming, possibly leading to contact with and compression of a spinal nerve root. Contact with a nerve can lead to intermittent lumbago.

One method of treating this type of disease consists in immobilizing the over- and underlying vertebrae by bone fusion while re-establishing the distance between the spinous processes and the lordosis angle of said vertebrae.

The implantable devices that are in the most widespread use in this method of surgical treatment comprise two rods connected to the over- and underlying vertebrae via screws positioned in the pedicles, with an osteosynthesis graft being applied to the vertebrae, the graft being positioned on the external portions of the screws and the rods.

That type of implantable device requires a large operating field to be opened, giving rise to necrosis in surrounding tissues of the patient that are handled in order to gain access to the pedicles and in order to put the screws and the graft into place.

Furthermore, the fastening points on the pedicles, using pedicular screws, are far away from the vertebral bodies on which the greatest loads are exerted. That configuration leads to a large lever arm, and thus to a transfer of the load applied initially to the pedicular screws, which can lead to them breaking. In order to remedy that drawback, and depending on the state of degeneration of the disk, those devices also have one or two inter-somatic cages inserted via the posterior, lateral, or anterior approach, thereby increasing the duration of surgery and thus increasing risks for the patient.

It has been found that the bone graft arranged in such cages shrinks in volume after being implanted, with the shrinkage being in particular by about 20%. Unfortunately, it is necessary for the bone graft to be mechanically stimulated by the vertebral bodies between which it is in contact in order for arthrodesis to be able to develop properly. With a rigid inter-somatic cage, it is therefore necessary to fill it with graft so that the bone graft projects beyond the ends of the cage. That configuration can make it more complicated to adjust lordosis and the distance between vertebrae.

WO 2013/123497 relates to an inter-spinous fusion device comprising a central body portion that is defined between first and second opposite lower walls, a rear wall, and first and second upper walls. The central body portion is open to its posterior portion, and can receive a graft only in the form of a solid block.

US 2012/0215262 relates to an osteosynthesis device for placing between the spinous processes. That device does not make it possible to achieve fusion between laminae.

U.S. Pat. No. 8,292,923 B1 relates to an implant for placing between the spinous processes. That implant likewise does not provide bearing between laminae and cannot be used to achieve fusion between laminae. In addition, it is not arranged to receive the spinous processes, at least in part. The central cavity occupies only a few millimeters and merely makes surface contact with the spinous processes.

There exists a need for a vertebral arthrodesis device for fusing together two adjacent vertebrae, in particular in the lumbar region, in particular for treating degenerative or accidental disk disease, but without requiring the use of screws and rods, so as to be able to reduce the operating field on the patient, thereby serving to diminish necrosis of the tissue surrounding the site of implantation.

There also exists a need for a vertebral arthrodesis device that enables the distance between the vertebrae and the lordosis angle between the overlying and underlying vertebrae to be adjusted in the vertebral region that is to be corrected.

OBJECT AND SUMMARY OF THE INVENTION

The present invention provides an implantable vertebral arthrodesis device for fusing together an underlying vertebra and an overlying vertebra, that mitigates the above-mentioned problems, and that advantageously comprises:

a) an anterior portion having an upper bearing zone suitable for receiving the lower portion of the upper lamina of the overlying vertebra and a lower bearing zone suitable for receiving the upper portion of the lower lamina of the underlying vertebra, the upper and lower bearing zones being spaced apart by a minimum height h, in order to maintain an intervertebral spacing;

b) rigid retaining devices arranged relative to the anterior portion in such a manner as to block migration of said anterior portion towards the spinal canal;

c) a posterior portion in connection with said anterior portion, comprising a main housing having first and second openings facing each other and suitable for receiving in part the spinous processes respectively of the underlying and overlying vertebrae; and d) granular osteosynthesis material arranged in said main housing.

The term "vertebral arthrodesis" is used to cover any arthrodesis performed on cervical vertebrae, or on dorsal or thoracic vertebrae, or on lumbar vertebra, or indeed on sacral vertebrae, and preferably on lumbar vertebrae.

One of skill understands by the term "posterior portion in connection with the anterior portion" that the posterior portion is secured to the anterior portion directly or via one or more parts other than the anterior portion.

Preferably, one of skill understands by the term "rigid element", in particular when referring to the retaining devices, and possibly to the anterior portion and/or to the posterior portion, or indeed to the partitioning element as defined below, any element that withstands deformation in operation sufficiently when loads are applied by the vertebrae, and regardless of the position of the vertebrae, in particular to ensure that pre-implantation dimensions are maintained after implantation, to within plus or minus 5%.

The retaining devices, and possibly the posterior portion and/or the anterior portion and/or the partitioning element as defined below are preferably selected to be made out of the following materials, singly or in combination: polyetheretherketone (PEEK) or its derivatives such as polyetherketon (PEK), titanium, polyethylene terephthalate (PET), carbon, hydroxapatite, incised human or animal bone.

The granular osteosynthesis material may be human and/or animal and/or artificial bone.

With human and/or animal bone, the granular osteosynthesis material may comprise cortico-spongy pads or shavings (possibly containing cortical bone and/or trabecular bone), calcified or decalcified bone derivatives.

With artificial bone, the granular osteosynthesis material may comprise phosphates, sulfates, or carbonates of tricalcium, or of hydroxapatite, or bone cement, such as ceramics or polymethyl methacrylate bone cements.

The anterior portion provides an implantable device with a bearing surface as far away as possible from the spinous processes, thereby serving to balance them.

The combination of maintaining intervertebral spacing by means of the anterior portion together with a posterior portion including a housing containing osteosynthesis material enables bone fusion to be achieved via the spinous processes, thereby limiting the extent to which the operative field needs to be opened on the patient.

The upper and lower spinous processes mechanically activate the granular osteosynthesis material placed in the main housing by passing through the first and second openings that lead into said main housing.

If a ligament is left in place during surgery between the spinous processes, then the implantable device of the invention may be used on its own without any posterior devices for securing the upper and lower spinous processes of said under- and overlying vertebrae to one another.

If the ligament between the spinous processes is removed, or if the practitioner so desires, the implantable device of the invention may be combined with a posterior securing device for securing said upper and lower spinous processes to each other. The posterior securing device may comprise an elongate element having first and second ends together with a securing device, preferably removable, for securing said ends together. Said elongate element is preferably arranged around the upper and lower spinous processes in the vertebral region that is to be corrected.

The posterior portion may be rigid or it may be made of a flexible material. If it is made of flexible material, the posterior portion is preferably combined with an elongate element having at its ends means for securing said ends together so as to exert action that is the opposite of that exerted by the spinous processes on the posterior portion made of a flexible material filled with osteosynthesis material while in the lordosis position. Said elongate element is preferably arranged around the spinous processes and thus around the posterior portion of the implantable device of the invention.

The anterior portion may be rigid, as defined below, or it may be made of flexible material, preferably out of a flexible strip as defined in the present specification. The flexible strip is preferably provided with first and second ends that are secured to the retaining devices and/or to the posterior portion and/or to said partitioning element (defined below).

Advantageously, the flexible strip co-operates with said partitioning element and/or said retaining devices and/or said posterior portion to define an auxiliary housing suitable for receiving a granular osteosynthesis material. This configuration enhances fusion between laminae.

In a variant embodiment, the implantable device of the invention includes a rigid partitioning element arranged between the anterior portion and the posterior portion.

Preferably, the partitioning element is arranged in a plane that is substantially parallel to the plane in which the anterior portion is arranged.

The arrangement of the partitioning element may restore anatomical spacing between vertebrae and may restore lordosis.

The partitioning element serves to give the implantable detect of the invention three bearing points between the laminae in combination with the anterior portion: two bearing points against the anterior portion and one bearing point against the partitioning element. This arrangement thus enables the implantable device of the invention to avoid its anterior portion tilting rewards against the spinous processes, thereby improving the stability of the device.

In a variant embodiment, the main housing is made of a flexible material, preferably a flexible strip having a first end and a second end that are secured respectively to the first lateral edge and to the second lateral edge of said anterior portion and/or of the retaining devices and/or of the partitioning element.

Advantageously, since the main housing is made of a material that is flexible and thus deformable, it is suitable for being subjected to micromovements in compression or in lordosis that stimulate the granular osteosynthesis material so as to facilitate bone fusion.

Advantageously, when the implantable device has a rigid partitioning element, the flexible material is preferably in connection with said partitioning element, either directly, or else via the retaining devices and/or the anterior portion.

When connected via the anterior portion, the main housing is C-shaped in its cross-section, with the ends of the C-shape being formed by the first and second ends of the flexible strip.

The partitioning element improves the strength of the main housing and avoids it having any tendency to collapse when filled with a granular osteosynthesis material.

The first and second ends of the flexible strip may be adhesively bonded to the first and second lateral edges of the anterior portion and/or of the retaining devices and/or of the partitioning element, or indeed they may be rolled up in two sheaths arranged on the retaining devices and/or the partitioning element.

The flexible strip may be made of at least one flexible biocompatible polymer material, and it may either be non-absorbable, i.e. it remains permanently in the body, or it may be semi-absorbable, i.e. only a portion of the flexible strip remains permanently in the body. The flexible strip may for example be a film of silicone or it may be made of a textile material, such as a non-woven material, a knit, a braid, or a woven material. The textile material may optionally be coated on its inside face and/or its outside face in a coating that is partially or totally absorbable or non-absorbable, e.g. made of silicone and/or polylactic acid of L or D form (PLLA or PDLA), or it may be made of a poly(lactic-co-glycolic acid) copolymer (PLGA).

The textile material is preferably made of one or more synthetic materials, and it may be made of polypropylene, polyethylene terephthalate (PET), a polyamide such as PA6-6, polytetrafluoroethylene (PTFE), a mixture of polypropylene and PTFE, or mixtures thereof.

In a variant embodiment, the retaining devices are supported by said partitioning element or the posterior portion.

In a variant embodiment, the partitioning element co-operates at least in part with the anterior portion to define an auxiliary housing having first and second openings facing each other, said auxiliary housing being suitable for receiving a granular osteosynthesis material, and being arranged in such a manner as to receive the laminae of said over- and underlying vertebrae in part.

Advantageously, in addition to bone fusion between spinous processes, the implantable device of the invention also makes it possible to achieve bone fusion between laminae. This provision improves bone fusion in the vertebral region to be corrected.

In a variant embodiment, the anterior portion comprises first and second lateral edges in connection with the first and second lateral edges of the partitioning element respectively via first and second lateral portions.

Preferably, the first and second ends of the flexible strip of the main housing are secured, e.g. by adhesive, to said first and second lateral portions, respectively.

In a subvariant, the first and second lateral portions diverge towards the anterior portion.

This provision makes it possible to optimize the volume of the auxiliary housing as defined, at least in part, between the anterior portion and the partitioning element, so that the quantity of osteosynthesis material placed in said auxiliary housing is as large as possible. The area of bone fusion, in particular between laminae, is thus optimized.

In a variant embodiment, the partitioning element and possibly the retaining devices is/are generally U-shaped or H-shaped.

This shape encourages receiving the laminae and the spinous processes in the main housing, and possibly in the auxiliary housing. This shape also improves the quantity of granular osteosynthesis material that can be received in the main housing, and possibly also in the auxiliary housing, thereby improving the quality of bone fusion.

This provision also makes it possible to give a pivot axis to the spinous process of the overlying vertebra, and possibility to receive the spinous process of the overlying vertebra without necessarily incising it.

In a variant embodiment, the posterior portion, in particular the rear wall, comprises a wall having an upper first recess, in particular of U-shape, and possibly a lower second recess, in particular of U-shape. Preferably, the posterior portion has a wall that is H-shaped.

The posterior portion as arranged in this way can receive the spinous processes at least in part without any need to incise them.

In a variant embodiment, the upper bearing zone of the anterior portion is convex in shape, and the lower bearing zone of the anterior portion is preferably concave in shape.

This provision enables the anterior portion to match the anatomical shape of the laminae of the over- and underlying vertebrae, thereby improving the ergonomics of said device.

In a variant embodiment, the anterior face of the anterior portion is concave.

This provision enables the anterior face of the anterior portion to be spaced apart from the dura mata, and avoids compressing the ligamentum flavum.

In a variant embodiment, the anterior portion slopes towards the main housing.

The anterior portion preferably forms an angle—with the bearing plane (P) on which the implantable device of the invention rests.

The angle · is preferably less than 90°, more preferably lies in the range 45° to 90°, and most particularly lies in the range 45° to 75°.

This provision favors adjusting the lordosis of the over- and underlying vertebrae.

This provision also improves the ergonomics of the device in that it is a better match to the arrangement of the over- and underlying vertebrae, which naturally form a staggered configuration.

In a variant embodiment, the lower bearing zone of the anterior portion comprises first and second feet sloping towards the main housing.

These feet serve to improve the stability of the bearing against the laminae of the underlying vertebrae.

In a variant embodiment, the retaining devices comprise at least one first upper projection and at least one first lower projection, which projections extend from the first and/or second lateral edge(s) of said partitioning element, and are provided at their ends with respective orifices for passing screws.

Preferably, said screws combined with said projections form posterior securing devices for securing the upper and lower spinous processes together.

This provision makes it possible to reduce the operative field on the patient, thereby limiting the extent of tissue necrosis. There is no need to use screws and rods secured to the pedicles, which are spaced apart anatomically from the spinous processes.

In a variant embodiment, the flexible strip is a textile panel, possibly coated in part in a coating, or it is made of a film of at least one polymer material.

Said coating may be continuous, such as a layer, or it may be discontinuous, in particular it may be arranged in the form of dots, lines, or geometrical patterns such as lozenges, for example.

In a variant embodiment, the anterior portion, the retaining devices, possibly the posterior portion, and/or the partitioning element are made as a single part, preferably by molding.

In a variant embodiment, the anterior portion, the retaining devices, possibly the posterior portion and/or the partitioning element are made of osteosynthesis material, as defined above, and in particular a non-granular material, e.g. molded hydroxyapatite.

This provision further improves the area of bone fusion, both between laminae and between spinous processes.

In a second aspect, the present invention also provides a set comprising an implantable device according to any one the above variant embodiments, and a posterior securing device for securing the upper and lower spinous processes together.

Preferably, said posterior securing device comprise an elongate element having first and second ends, and further comprise a securing device, preferably removable securing device, for securing said ends together.

Such posterior securing device may be the implantable device described in FR 2 961 687 A1.

DETAILED DESCRIPTION OF THE DRAWINGS

The present invention can be better understood on reading about the following three embodiments mentioned in non-limiting manner and described with reference to the following figures, accompanying these presents, in which.

DETAILED DESCRIPTION OF EMBODIMENTS

Figure 1A:
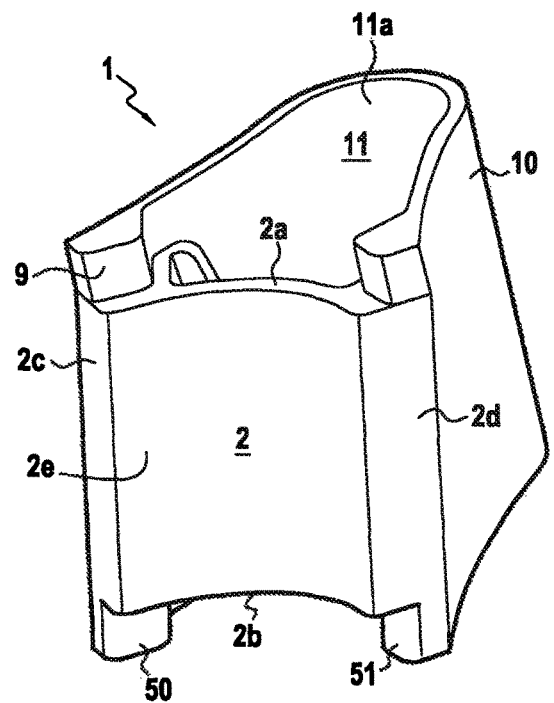
FIGS. 1A and 1B are diagrammatic perspective views of a first embodiment of an implantable device of the invention.
Figure 1B:
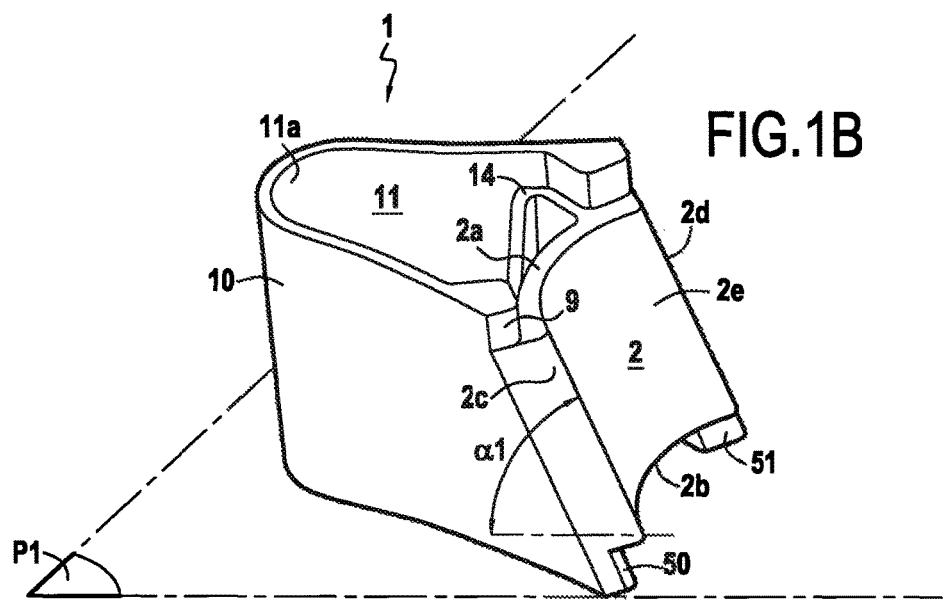

The first embodiment of an implantable vertebra artherodesis device 1 for fusing together two vertebrae, i.e. an overlying vertebra and an underlying vertebra, as shown in FIGS. 1A, 1B, 2, 3, and 4, comprises an anterior portion 2 having a top bearing zone 2a for receiving at least part of the bottom portion 3 of the top lamina 4 of the overlying vertebra 5 and a bottom bearing zone 2b suitable for receiving the top portion 6 of the bottom lamina 7 of the underlying vertebra 8, the top and bottom bearing zones 2a and 2b being spaced apart by a minimum height h1 in order to maintain an intervertebral spacing. The implantable device 1 also has rigid retaining devices 9 arranged relative to the anterior portion 2 so as to block migration of said anterior portion 2 towards the spinal canal.

The implantable device 1 also has a posterior portion 10 in connection with said anterior portion 2, including a main housing 11 having first and second openings 11a and 11b facing each other and suitable for receiving in part the top and bottom spinous processes 12 and 13 respectively of the overlying and underlying vertebrae 5 and 8. At the time of implantation, the main housing 11 is filled with a granular osterosynthesis material (not shown).

In this particular element, the anterior and posterior portions 2 and 10 are rigid.

The implantable device 1 includes a rigid partitioning element 14 arranged between the anterior portion 2 and the posterior portion 10, in particular in a plane that is substantially parallel to the plane in which the anterior portion 2 is arranged.

Figure 2:
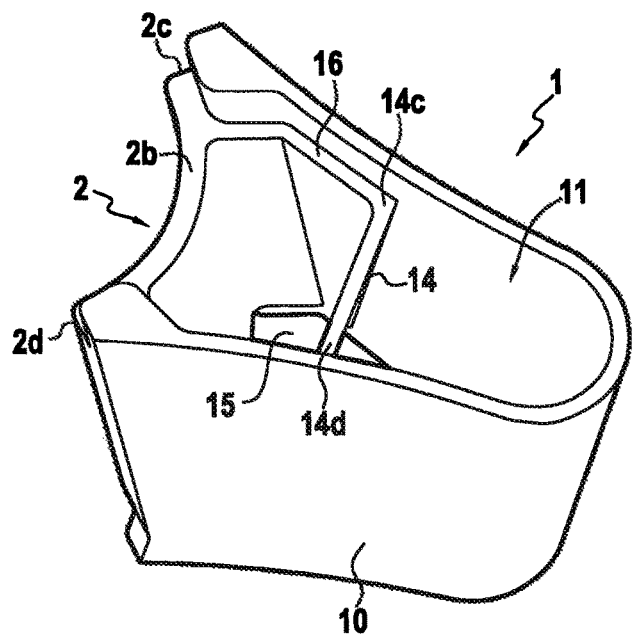
FIG. 2 is a diagrammatic view from beneath of the first embodiment of an implantable device of the invention as shown in FIGS. 1A and 1B.

In this particular element, the retaining devices 9 extend the posterior portion 10 over the anterior portion 2, as can be seen in FIG. 2.

The partitioning element 14 co-operates, at least in part with the anterior portion 2, to define an auxiliary housing 15 having first and second openings 15a and 15b facing each other, said auxiliary housing 15 receiving in operation a granular osteosynthesis material (not shown) and being arranged in such a manner as to receive in part the laminae 4, 7 of said underlying and overlying vertebrae 5 and 8.

The anterior portion 2 has first and second lateral edges 2c and 2d connected to the first and second lateral edges 14c and 14d of the partitioning element 14 via respective first and second lateral portions 16 and 17. Preferably, the first and second lateral portions 16 and 17 diverge towards the anterior portion 2.

Figure 3:
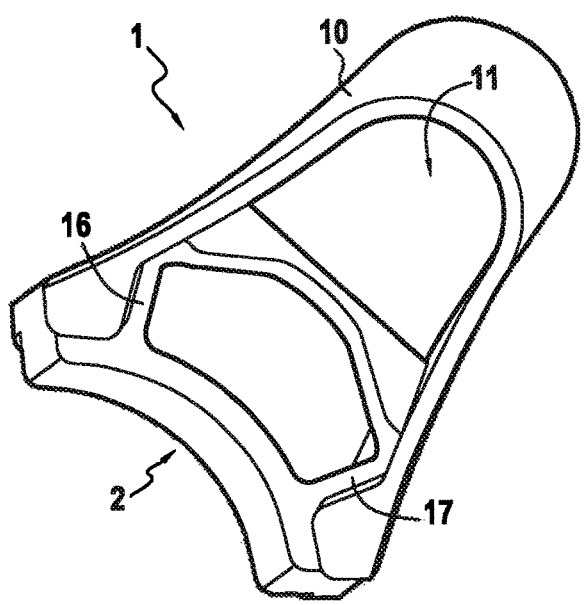
FIG. 3 is a diagrammatic view seen from above of the first embodiment of an implantable device of the invention as shown in FIGS. 1A, 1B, and 2.

The partitioning element 14 is generally U-shaped, as can be seen in FIG. 3. In this particular example, the posterior portion 10, the retaining devices 9, the partitioning element 14, and the posterior portion 2 are a single molded part, e.g. made of PEEK or hydroxyapatite.

The top bearing zone 2a of the anterior portion 2 is convex in shape; preferably the bottom bearing zone 2b of the anterior portion 2 is concave in shape.

The anterior portion 2 has an anterior face 2e that is concave. The anterior portion 2 slopes towards said partitioning element 14, and in particular forms an angle ·1 with the bearing plane (P1) on which the implantable device 1 rests, where ·1 is less than 90°, preferably lying in the range 45° to 90°.

The lower bearing zone 2b of the anterior portion 2 has first and second feet 50 and 51 sloping towards the main housing 11.

In operation, granular osteosynthesis material is arranged in the auxiliary and main housings 15 and 11, preferably so as to project from said housings 11 and 15 in order to mitigate the observed 20% shrinkage in volume.

Figure 4:
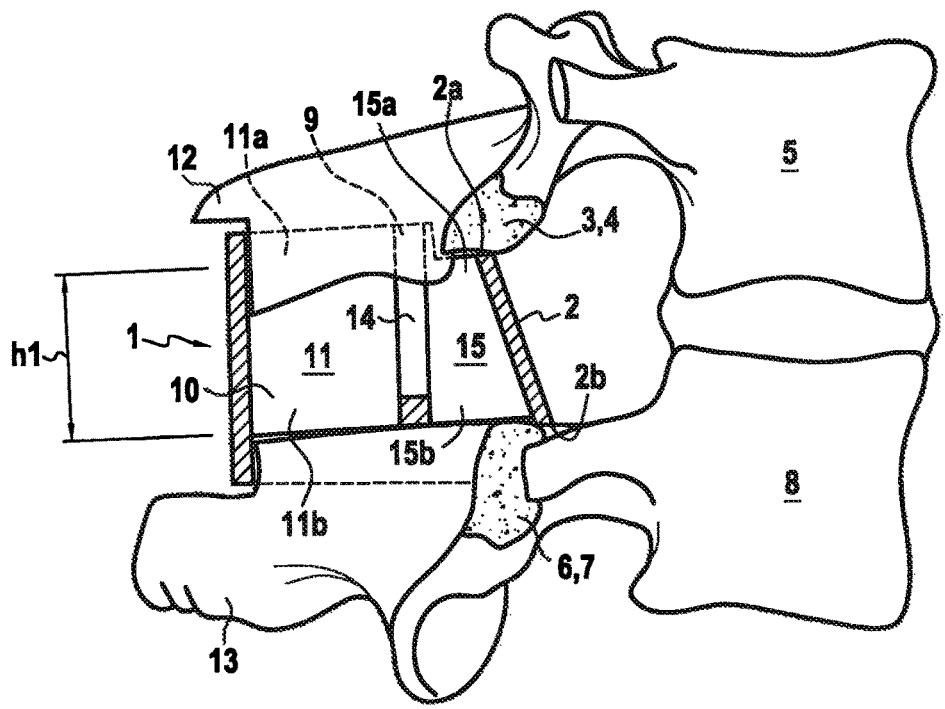
FIG. 4 is a diagrammatic view of a first embodiment of a device of the invention shown in operation in position between overlying and underlying vertebrae, with portions of the device being cut away.

The implantable device 1 then has the anterior portion 2 placed between the laminae 4 and 7 and the posterior portion 10 placed between the upper and lower spinous processes 12 and 13, as shown in FIG. 4. The spinous processes 12 and 13 may optionally be incised, as shown in FIG. 4, so as to penetrate better into said main housing 11 and so as to come into contact with the osteosynthesis material.

The anterior portion 2 serves to adjust intervertebral spacing. The partitioning element 14 improves the stability of the anterior portion 2 and prevents it from tilting towards the spinous processes 12, 13. The areas of contact between the osteosynthesis material and the upper and lower laminae 4 and 7, and between the osteosynthesis material and the upper and lower spinous processes 12 and 13 are large, thereby encouraging bone fusion beyond merely the spinous processes 12, 13.

Figure 5:
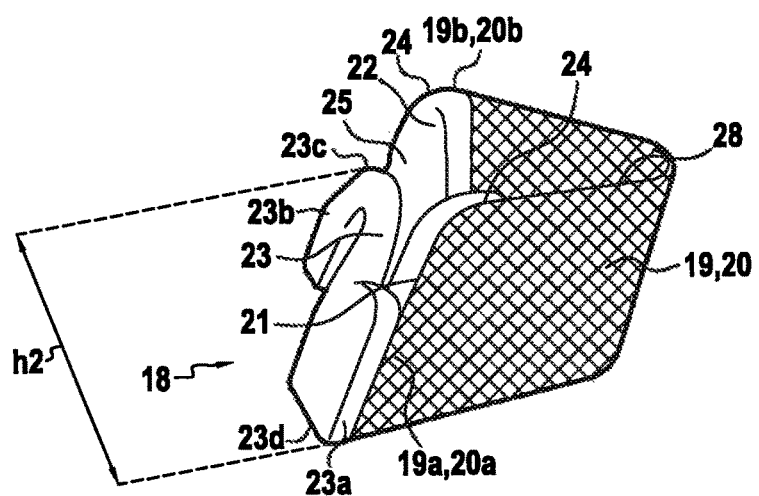
FIG. 5 is a diagrammatic perspective view of a second embodiment of a device of the invention.
Figure 6:
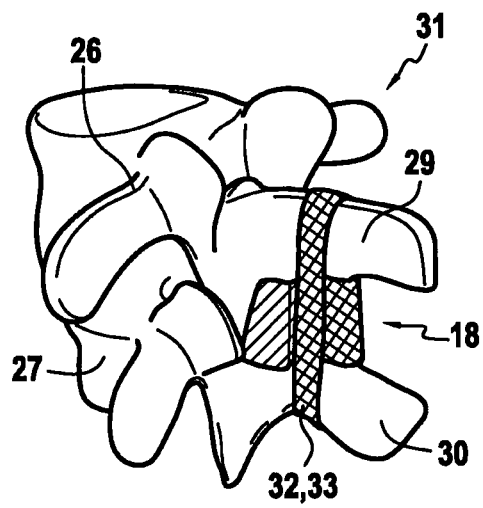
FIG. 6 is a diagrammatic perspective view of a first embodiment of a set of the invention comprising the second embodiment of the implantable device as shown in FIG. 5 together with posterior link device linking together the upper and lower spinous processes.
Figure 7:
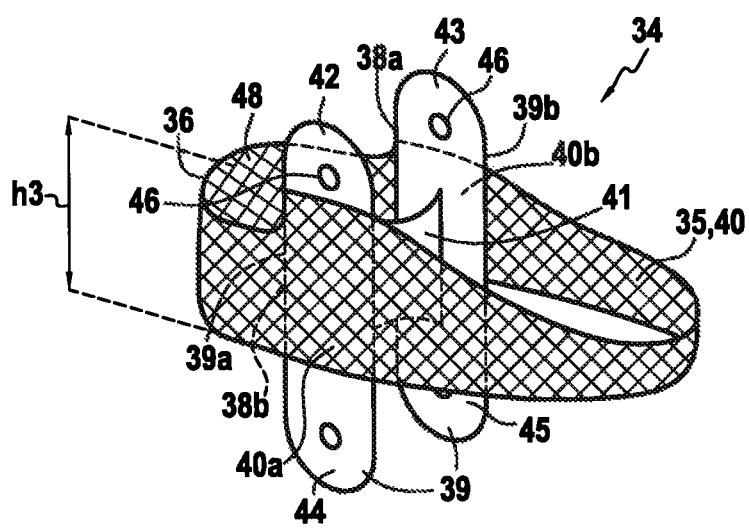
FIG. 7 is a diagrammatic perspective view of a third embodiment of an implantable device of the invention.

The second embodiment of the implantable device 18 shown in FIGS. 5 and 6 is described below only for its differences compared with the first embodiment of an implantable device 1. The posterior portion 19 is made of a flexible material, in particular of a flexible strip 20 having a first end 20a and a second end 20b that are secured respectively to the first and second edges 25a and 25b of said partitioning element 25, and also respectively to the first and second lateral portions 21 and 22 connecting the first and second lateral edges 23a and 23b of the anterior portion 23 to the edges 25a and 25b of said partitioning element 25.

The anterior portion 23 serves to maintain vertebral spacing at a height h2 via the upper and lower bearing zones 23c and 23d.

In this example, the retaining devices 24 are supported by the partitioning element 25. The partitioning element 25 and the retaining devices 24 are thus generally U-shaped. The anterior portion 23, the partitioning element 25, and the retaining devices 24 are rigid, and in this particular embodiment they are made as a single part, e.g. by molding PEEK or hydroxyapatite.

In operation, the second embodiment of an implantable device 18 is placed between over- and underlying vertebrae 26 and 27 in the same manner as the first embodiment of an implantable device 1. Since the main housing 28 is made of a flexible material, such as a textile panel, it enables the spinous processes 29, 30 make greater contact with the osteosynthesis material during lordosis movements of the spine, thereby encouraging activation of the bone graft and the formation of bone fusion.

FIG. 6 shows a first embodiment of a set 31 of the invention comprising the implantable device 18 shown in FIG. 5. The set 31 thus comprises a posterior securing device 32 for securing the upper and lower spinous processes 29 and 30 to each other. The posterior securing device 32 comprise an elongate element 33 having first and second ends and a device for securing said ends to each other. Said posterior securing device 32 may be removable, as described in FR 2 961 687 A1. In this particular embodiment, the elongate element 32 surrounds the upper and lower spinous processes 29 and 30 and also the posterior portion 19 containing the granular osteosynthesis material. The elongate element 33 thus contributes to holding the granular osteosynthesis material in the main housing 28, in particular when the spine is in extension.

The third embodiment of an implantable device 34 of the invention is described below only for its differences relative to the first embodiment of an implantable device 1. The third embodiment of an implantable device 34 has a posterior portion 35 and an anterior portion 36 that are both made of flexible material. The anterior portion 36 is made of a flexible strip 38 having first and second ends 38a and 38b that are secured respectively to the first edge 39a and to the second edge 39b of the retaining devices 29. Likewise, the posterior portion 35 is made of a flexible strip 40 having first and second ends 40a and 40b that are secured respectively to the first edge 39a and to the second 39b of the retaining devices 39.

Together, the partitioning element 41 and the retaining devices 39 are generally H-shaped. The retaining devices 39 comprise first and second upper projections 42 and 43 and first and second lower projections 44 and 45 respectively extending the first and second lateral edges 39a and 39b of said retaining devices 39. Each of these projections 42 to 45 is provided with at least one orifice 46 suitable for co-operating with a screw (not shown). Said projections 42 to 45 and the screws thus form posterior securing devices 47 for securing the implantable device 34 to the upper and lower spinous processes.

The provision of an osteosynthesis material in sufficiently compacted manner in the auxiliary housing 48 defined between the anterior portion 36 and the partitioning element 41 enables upper and lower bearing zones 35a and 35b to be formed that are suitable for coming into contact with the upper and lower laminae and thus serves to maintain minimum vertebral spacing, corresponding to the minimum height h2 of the anterior portion 36.

The at least partial deformation of the auxiliary housing 48 serves to improve bone fusion, since the osteosynthesis material is stimulated to a greater extent by the over- and underlying vertebral laminae in the vertebral region that is to be corrected.

The invention claimed is:

1. An implantable vertebral arthrodesis device for fusing together an underlying vertebra and an overlying vertebra, the device comprising:
   a) an anterior portion having an upper bearing zone suitable for receiving a lower portion of an upper lamina of the overlying vertebra and a lower bearing zone suitable for receiving an upper portion of a lower lamina of the underlying vertebra, the upper and lower bearing zones being spaced apart by a minimum height h, in order to maintain an intervertebral spacing;
   b) rigid retaining devices arranged relative to the anterior portion in such a manner as to block migration of said anterior portion towards the spinal canal;
   c) a posterior portion in connection with said anterior portion, comprising a main housing having first and second openings facing each other and suitable for receiving in part the spinous processes respectively of the underlying and overlying vertebrae;
   d) a rigid partitioning element arranged between the anterior portion and the posterior portion that co-operates, at least in part with the anterior portion, to define an auxiliary housing having first and second openings facing each other and arranged in such a manner as to be configured to receive in part the laminae of said underlying and overlying vertebrae; and
   e) granular osteosynthesis material arranged in said main housing and said auxiliary housing.

2. The implantable device according to claim 1, wherein each of the anterior portion, the retaining devices and the partitioning element has a first lateral edge and a second lateral edge, and wherein the main housing is made of a flexible strip having a first end and a second end that are secured respectively to the first lateral edge and to the second lateral edge of said anterior portion and/or of said retaining devices and/or of said partitioning element.

3. The implantable device according to claim 1, wherein the retaining devices are supported by said partitioning element.

4. The implantable device according to claim 1, wherein the retaining devices are supported by said posterior portion.

5. The implantable device according to claim 1, wherein the anterior portion comprises first and second lateral edges in connection with first and second lateral edges of the partitioning element respectively via first and second lateral portions.

6. The implantable device according to claim 5, wherein the first and second lateral portions diverge towards the anterior portion.

7. The implantable device according to claim 1, wherein the partitioning element is generally U-shaped or H-shaped.

8. The implantable device according to claim 1, wherein the upper bearing zone of the anterior portion is convex in shape.

9. The implantable device according to claim 1, wherein the lower bearing zone of the anterior portion is concave in shape.

10. The implantable device according to claim 1, wherein the anterior portion has an anterior face that is concave.

11. The implantable device according to claim 1, wherein the anterior portion slopes towards said partitioning element.

12. The implantable device according to claim 1, wherein the lower bearing zone of the anterior portion comprises first and second feet sloping towards the main housing.

13. The implantable device according to claim 1, wherein each of said partitioning element and said retaining devices has a first lateral edge and a second lateral edge and wherein the retaining devices comprise at least one first upper projection and at least one first lower projection, which projections extend from the first and/or second lateral edge(s) of said partitioning element, and/or of said retaining devices, and are provided at their ends with respective orifices for passing screws.

14. The implantable device according to claim 1, wherein the anterior portion and the retaining devices are made of osteosynthesis material.

15. The implantable device according to claim 14, wherein the posterior portion and the partitioning element are made of osteosynthesis material.

16. A set comprising an implantable device according to claim 1, and a posterior securing device for securing together the upper and lower spinous processes.

17. A set according to claim 16, wherein the posterior securing device comprises an elongate element having first and second ends, and a securing device for securing said ends together.

* * * * *